United States Patent
Ogata et al.

(10) Patent No.: US 9,057,997 B2
(45) Date of Patent: Jun. 16, 2015

(54) MOVING OBJECT DETECTING DEVICE, POWER SUPPLY CONTROL DEVICE, AND IMAGE PROCESSING APPARATUS

(75) Inventors: Kenta Ogata, Kanagawa (JP); Motofumi Baba, Kanagawa (JP); Kazuhiko Narushima, Kanagawa (JP); Masafumi Ono, Kanagawa (JP); Kouichi Azuma, Kanagawa (JP); Susumu Yamashina, Kanagawa (JP); Kenji Kuroishi, Kanagawa (JP); Keiko Shiraishi, Kanagawa (JP); Hidenori Horie, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 141 days.

(21) Appl. No.: 13/545,388

(22) Filed: Jul. 10, 2012

(65) Prior Publication Data
US 2013/0250372 A1    Sep. 26, 2013

(30) Foreign Application Priority Data

Mar. 21, 2012  (JP) ................................ 2012-064447

(51) Int. Cl.
| | |
|---|---|
| G03G 15/00 | (2006.01) |
| A61B 5/103 | (2006.01) |
| B60K 35/00 | (2006.01) |
| H04N 1/00 | (2006.01) |

(52) U.S. Cl.
CPC .......... *G03G 15/5004* (2013.01); *A61B 5/1036* (2013.01); *B60K 35/00* (2013.01); *H04N 1/00323* (2013.01); *H04N 1/00896* (2013.01); *H04N 1/00912* (2013.01); *H04N 2201/0094* (2013.01); *G03G 15/5016* (2013.01)

(58) Field of Classification Search
CPC ........................................................ G06F 1/26
USPC ................. 358/442, 1.15; 235/440; 73/865.4, 73/866.3
See application file for complete search history.

(56) References Cited

U.S. PATENT DOCUMENTS

| | | | | |
|---|---|---|---|---|
| 2006/0184780 | A1* | 8/2006 | Yamada et al. | 713/1 |
| 2011/0191950 | A1* | 8/2011 | Liu | 4/233 |
| 2011/0220648 | A1* | 9/2011 | Yang et al. | 220/211 |
| 2013/0299582 | A1* | 11/2013 | Ozawa et al. | 235/440 |
| 2013/0311035 | A1* | 11/2013 | Czyz et al. | 701/36 |

FOREIGN PATENT DOCUMENTS

| | | | | |
|---|---|---|---|---|
| JP | A-05-45471 | | 2/1993 | |
| JP | A-07-114308 | | 5/1995 | |
| JP | B2-4077440 | | 4/2008 | |
| WO | 2011-093340 | * | 8/2011 | ........... G06K 7/0091 |

* cited by examiner

Primary Examiner — Jerome Grant, II
(74) Attorney, Agent, or Firm — Oliff PLC

(57) ABSTRACT

A moving object detecting device includes a detecting device body that includes a detection unit formed in a chassis covering the inside of an apparatus and disposed to correspond to a monitoring window of which at least an aperture area or an aperture size is restricted and which monitors a moving object approaching the apparatus and a circuit board unit controlling a signal output from the detection unit and is disposed so that some optical axes among optical axes having detection surfaces of plural infrared detecting elements included in the detection unit, as focal points passes through the monitoring window and the other optical axes are blocked by the chassis, and an optical member that is formed in an inner wall of the chassis and that deflects the other optical axes of the infrared detection elements to pass through the monitoring window.

12 Claims, 14 Drawing Sheets

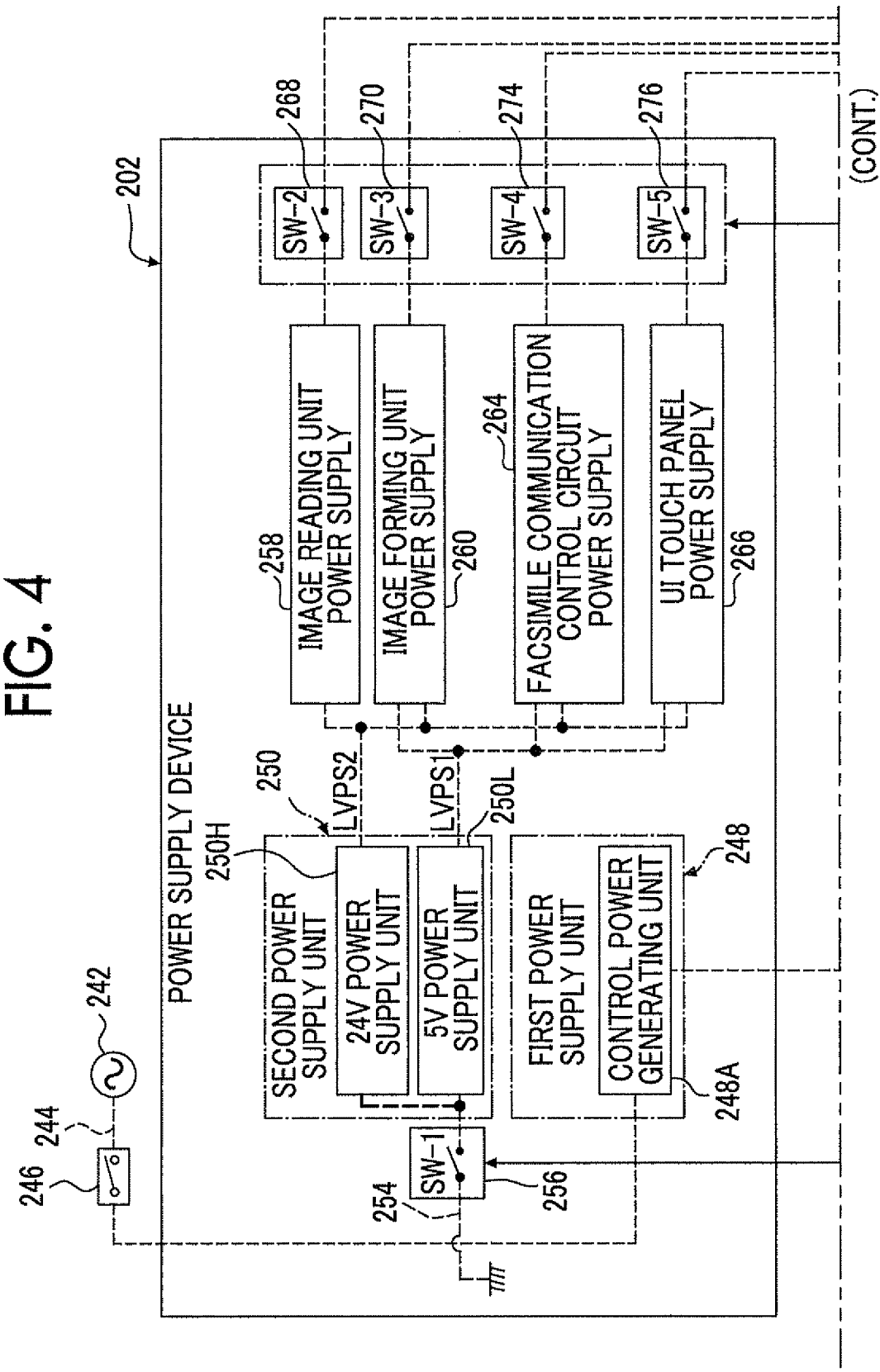

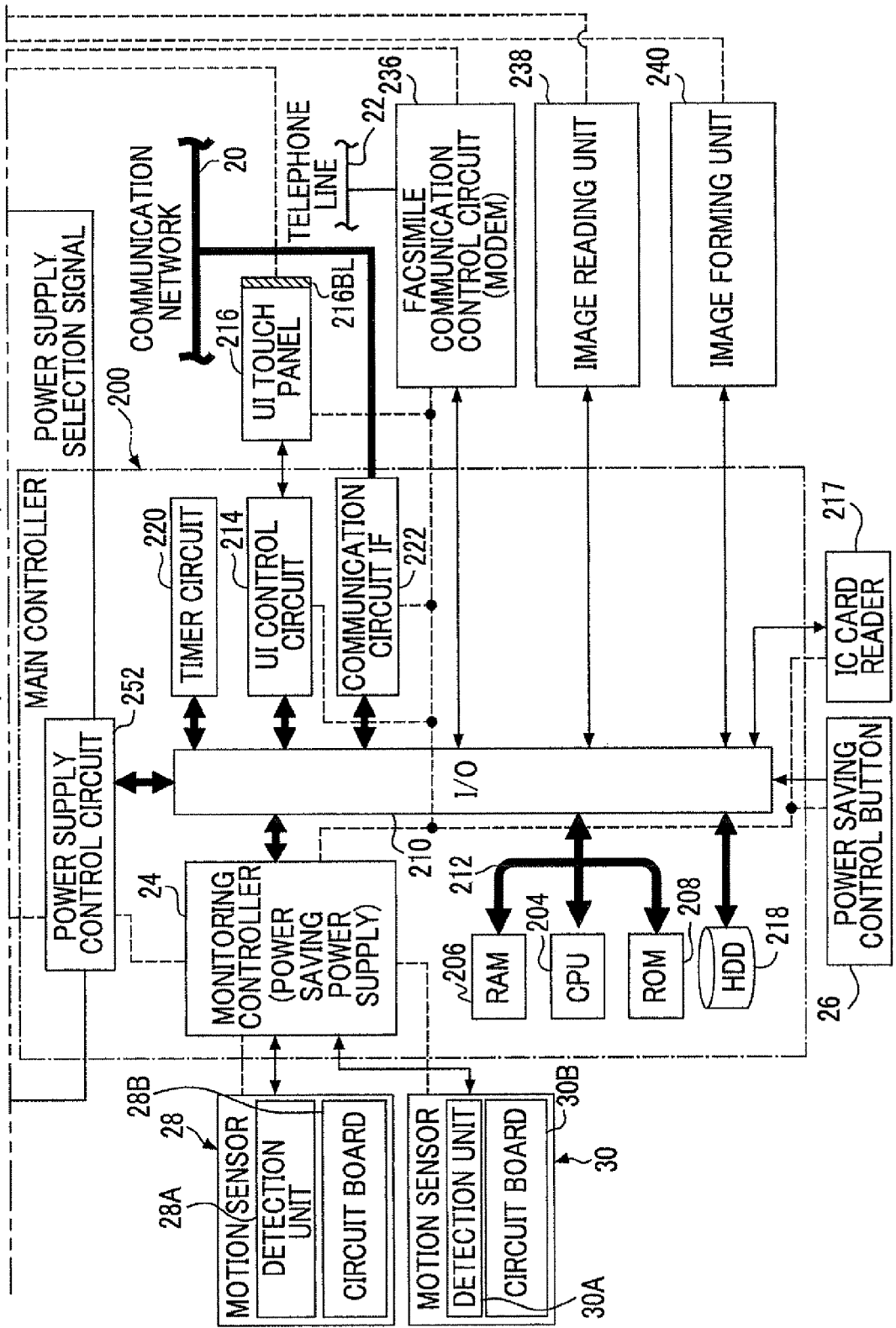
(FIG. 4 Continued)

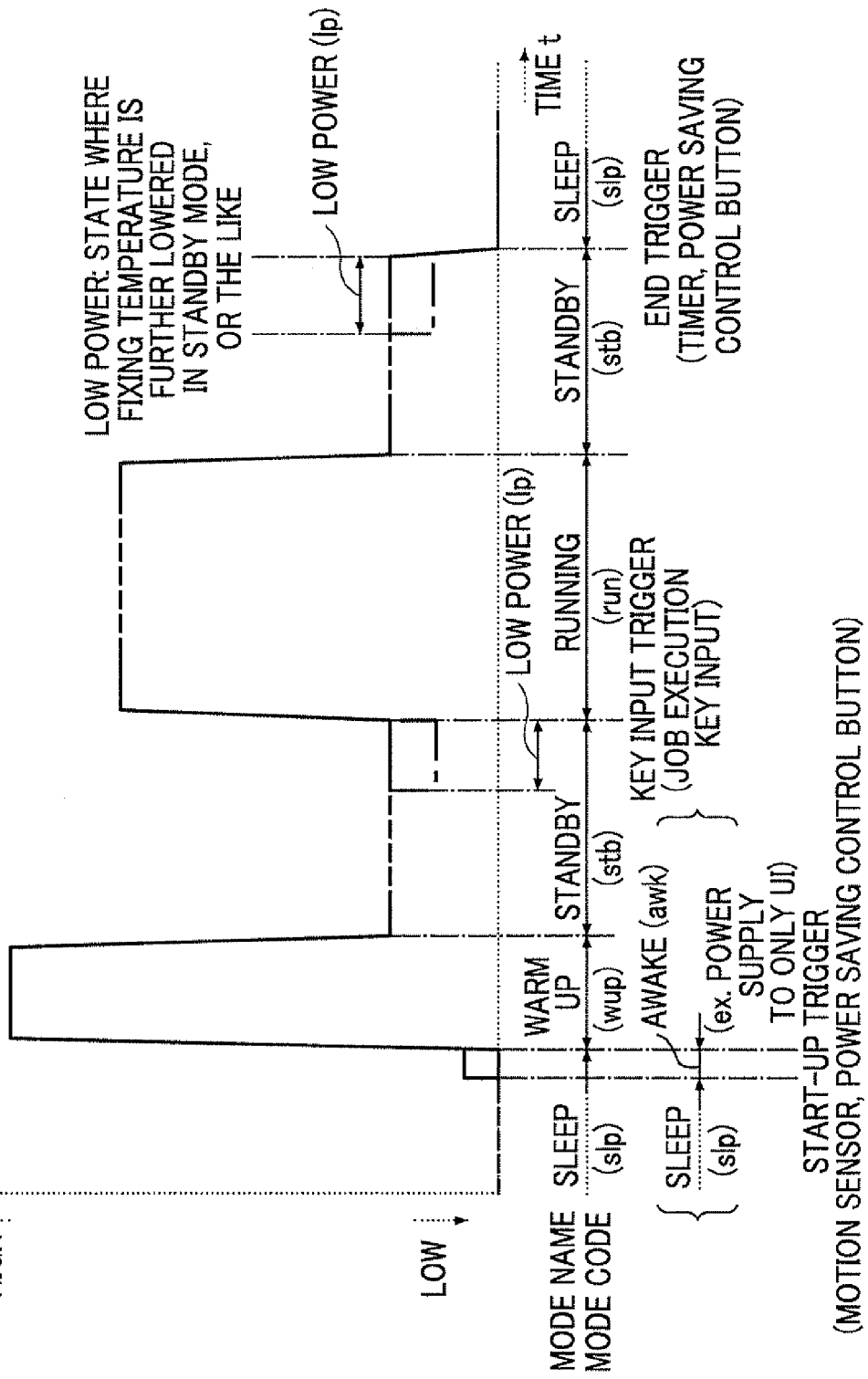

MOVING OBJECT DETECTING DEVICE, POWER SUPPLY CONTROL DEVICE, AND IMAGE PROCESSING APPARATUS

CROSS-REFERENCE TO RELATED APPLICATION

This application is based on and claims priority under 35 USC 119 from Japanese Patent Application No. 2012-064447 filed Mar. 21, 2012.

BACKGROUND (i) Technical Field

The present invention relates to a moving object detecting device, a power supply control device, and an image processing apparatus.

(ii) Related Art

For example, a pyroelectric type sensor (also referred to as a "pyroelectric sensor") which can detect movement of a person or the like using temperature change characteristics through detection of infrared rays is known as a sensor spatially detecting a subject (a moving object). The pyroelectric type sensor includes plural detection elements (hereinafter, also collectively referred to as a "detection element group") detecting infrared rays and a lens cover having infrared detection faces of the detection elements as focal positions are attached to the detection element groups having optical axes parallel to each other. Accordingly, in the pyroelectric type sensor, the overall detection area spreads from a detection base point (the detection element group) due to the optical functions of the lens cover and the detection area spreads further the farther it goes.

Here, in order to restrict the detection area (including a spreading width or a distance) of the pyroelectric type sensor to a specific area (to give directivity to the detection area), the pyroelectric sensor is disposed inside a wall without being exposed and through-holes (detection holes) enabling some optical axes of the plural detection elements to pass through the wall to the outside are formed. As the number of detection elements effectively used increases, the detection accuracy of the pyroelectric type sensor increases.

SUMMARY

According to an aspect of the invention, there is provided a moving object detecting device including: a detecting device body that includes a detection unit formed in a chassis covering the inside of an apparatus and disposed to correspond to a monitoring window of which at least an aperture area or an aperture size is restricted and which monitors a moving object approaching the apparatus and a circuit board unit controlling a signal output from the detection unit and that is disposed so that some optical axes among optical axes having detection surfaces of plural infrared detecting elements, which are included in the detection unit, as focal points pass through the monitoring window and the other optical axes are blocked by the chassis; and an optical member that is formed in an inner wall of the chassis and that deflects the other optical axes of the infrared detection elements to pass through the monitoring window.

BRIEF DESCRIPTION OF THE DRAWINGS

Exemplary embodiments of the present invention will be described in detail based on the following figures, wherein:

FIG. 4 is a schematic diagram functionally illustrating a main controller and a control system of a power supply device according to the exemplary embodiment;

FIG. 5 is a timing diagram illustrating modes and events serving as triggers of change to the modes in the image processing apparatus;

FIG. 10A is a front view of detection elements and FIG. 10B is a front view of a lens cover;

DETAILED DESCRIPTION OF THE EMBODIMENTS

Figure 1:
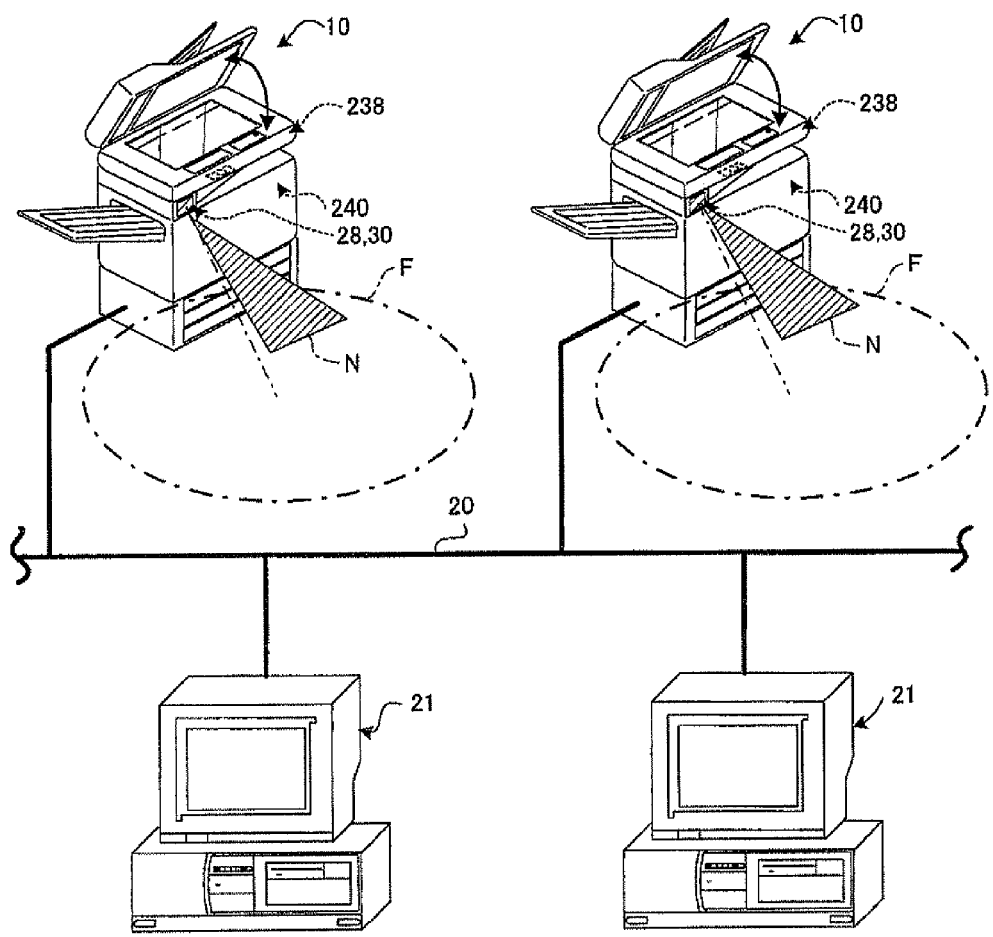
FIG. 1 is a diagram illustrating a communication network including an image processing apparatus according to an exemplary embodiment of the invention.

As shown in FIG. 1, an image processing apparatus 10 according to an exemplary embodiment is connected to a communication network 20 such as the Internet. In FIG. 1, two image processing apparatuses 10 are connected, but the number of image processing apparatuses is not limited. The number of image processing apparatuses may be one or three or more.

Plural PCs (Personal Computers) 21 as information terminal devices are connected to the communication network 20. In FIG. 1, two PCs 21 are connected, but the number of PCs is not limited. The number of PCs may be one or three or more. The information terminal device is not limited to the PC 21 and does not have to be connected in a wired manner. That is, a communication network transmitting and receiving information in a wireless manner may be employed.

As shown in FIG. 1, in the image processing apparatus 10, for example, data is remotely transmitted to the image processing apparatus 10 from the PC 21 to instruct to form (print) an image, or a user stands in front of the image processing apparatus 10 and instructs to perform various processes such as a copying process, a scanning (image reading) process, and a facsimile transmission and reception process through the use of various operations.

Figure 2:
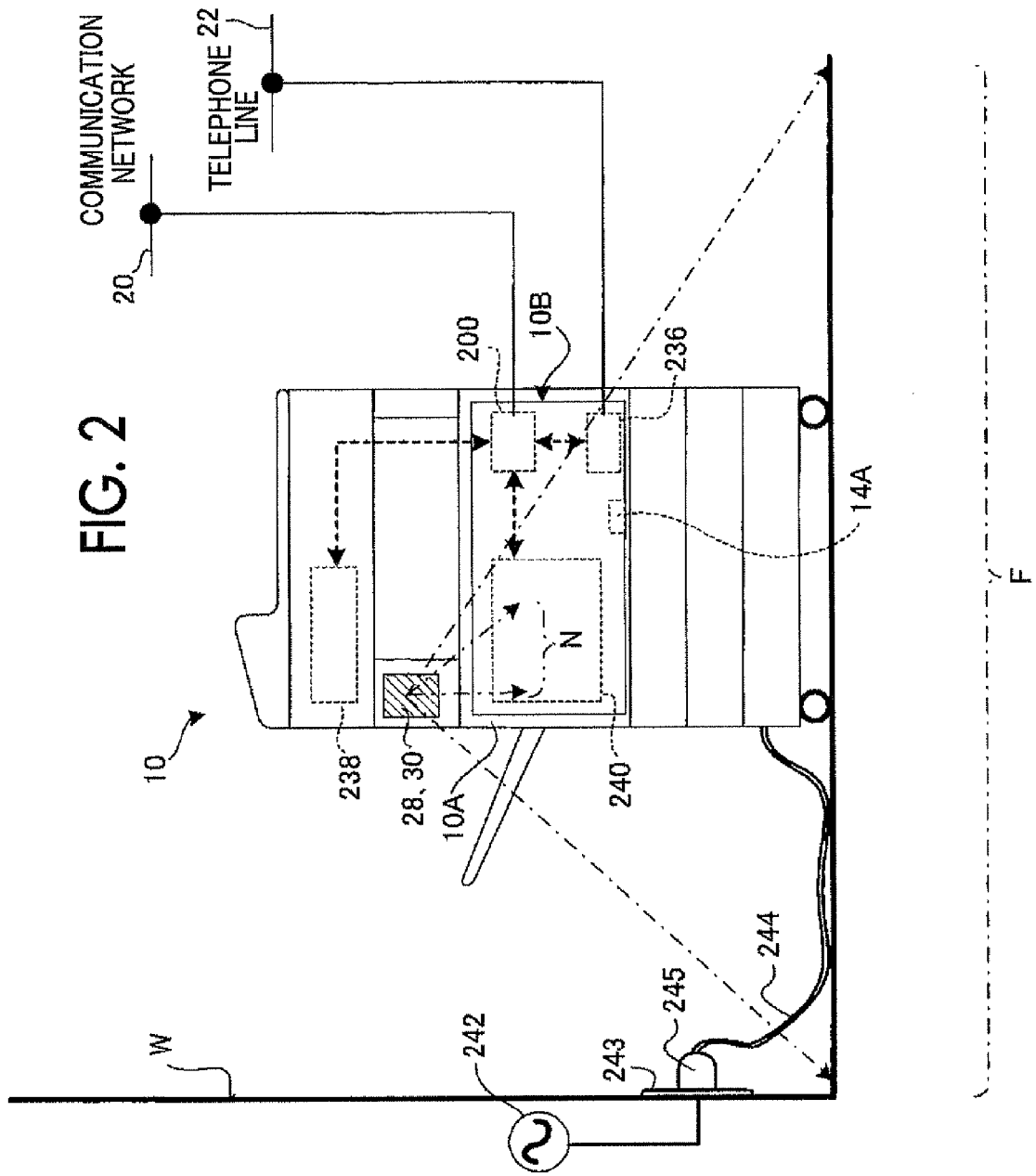
FIG. 2 is a diagram schematically illustrating the image processing apparatus according to the exemplary embodiment.

FIG. 2 shows the image processing apparatus 10 according to this exemplary embodiment.

The image processing apparatus 10 includes an image forming unit 240 forming an image on a recording sheet, an image reading unit 238 reading an image of an original document, and a facsimile communication control circuit 236. The image processing apparatus 10 also includes a main controller 200, which controls the image forming unit 240, the image reading unit 238, and the facsimile communication control circuit 236 to primarily store image data of the image of the original document read by the image reading unit 238 or to transmit the read image data to the image forming unit 240 or the facsimile communication control circuit 236.

A communication network 20 such as the Internet is connected to the main controller 200 and a telephone line 22 is connected to the facsimile communication control circuit 236. The main controller 200 is connected to a host computer, for example, via the communication network 20 and serves to receive image data or to perform facsimile reception and facsimile transmission through the use of the facsimile communication control circuit 236 via the telephone line 22.

The image reading unit 238 includes a platen on which an original document is positioned, a scanning driving system scanning an image of the original document placed on the platen and irradiating the image with light, and a photoelectric conversion device such as a CCD receiving light reflected or transmitted through the use of the scanning driving system and converting the light into an electric signal.

The image forming unit 240 includes a photosensitive member. A charging device uniformly charging the photosensitive member, a scanning exposure unit applying a light beam on the basis of image data, an image developing unit developing an electrostatic latent image formed through the scanning exposure of the scanning exposure unit, a transfer unit transferring the developed image on the photosensitive member onto a recording sheet, and a cleaning unit cleaning the surface of the photosensitive member after the transfer are arranged around the photosensitive member. A fixing unit fixing the image on the recording sheet after the transfer is disposed in a transport path of the recording sheet.

In the image processing apparatus 10, a plug 245 is attached to a tip of an input power supply line 244. By inserting the plug 245 into a wiring plate 243 of a commercial power source 242 wired to the wall surface W, the image processing apparatus 10 is supplied with power from the commercial power source 242.

Hardware Configuration of Control System of Image Processing Apparatus

Figure 3:
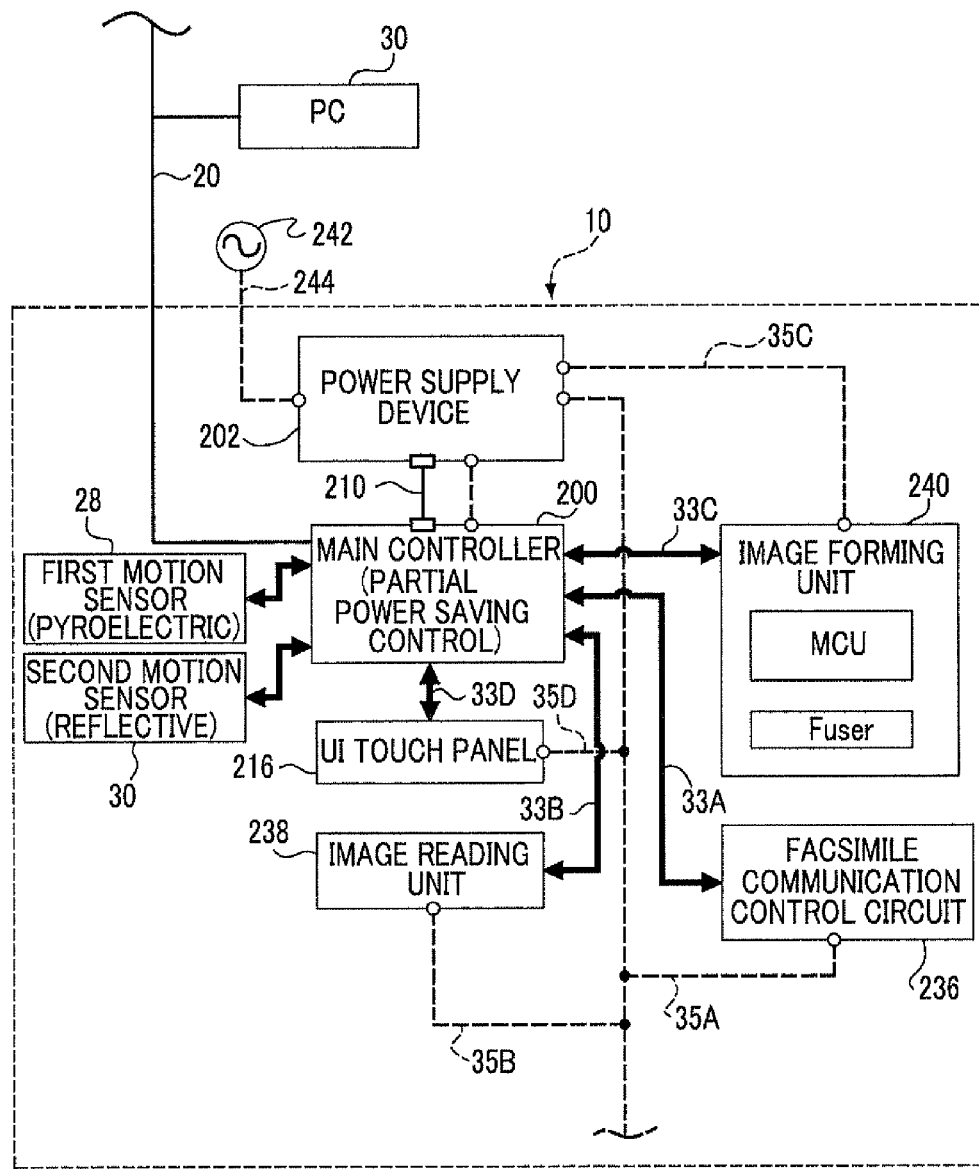
FIG. 3 is a block diagram illustrating the configuration of a control system of the image processing apparatus according to the exemplary embodiment.

FIG. 3 is a schematic diagram illustrating the hardware configuration of a control system of the image processing apparatus 10.

The communication network 20 is connected to the main controller 200. The facsimile communication control circuit 236, the image reading unit 238, the image forming unit 240, and an UI touch panel 216 are connected to the main controller 200 via buses 33A to 33D such as data buses or control buses. That is, the main controller 200 as a main body controls the units of the image processing apparatus 10. The UI touch panel 216 may be provided with a UI touch panel backlight 216BL (see FIG. 4).

The image processing apparatus 10 includes a power supply device 202, which is connected to the main controller 200 via a signal harness 201.

The power supply device 202 is supplied with power from the commercial power source 242.

The power supply device 202 is provided with power supply lines 35A to 35D independently supplying power to the main controller 200, the facsimile communication control circuit 236, the image reading unit 238, the image forming unit 240, and the UI touch panel 216, respectively. Accordingly, the main controller 200 may individually supply power to the units (devices) (power supply mode) or may block the supply of power thereto (sleep mode), thereby performing a so-called partial power-saving control.

Two motion sensors of a first motion sensor 28 and a second motion sensor 30 are connected to the main controller 200 and monitors the presence of a person around the image processing apparatus 10. The first motion sensor 28 and the second motion sensor 30 will be described later.

Functional Block Diagram of Partial Power-Saving Configuration

FIG. 4 is a schematic diagram mainly illustrating the units (also referred to as "devices" or "modules") controlled by the main controller 200 and power supply lines of the power supply device 202 supplying power to the main controller 200 and the devices. In this exemplary embodiment, the image processing apparatus 10 may supply power or may block the supply of power by the units (partial power saving).

The partial power saving by the units is an example. The units may be classified into several groups and may perform the power-saving control by the groups or may collectively perform the power-saving control on the units.

Main Controller

As shown in FIG. 4, the main controller 200 includes a CPU 204, a RAM 206, a ROM 208, an I/O (input and output unit) 210, and a bus 212 such as a data bus or a control bus connecting them. The I/O 210 is connected to the UI touch panel 216 (including the backlight unit 216BL) via a UI control circuit 214. The I/O 210 is also connected to a hard disk (HDD) 218. By causing the CPU 204 to operate on the basis of a program stored in the ROM 208 or the hard disk 218, the functions of the main controller 200 are embodied. By installing the program from a recording medium (such as a CD, a DVD, a BD (Blu-ray Disc), a USB memory, and an SD memory) storing the program and causing the CPU 204 to operate on the basis of the program, the image processing functions may be embodied.

The I/O 210 is also connected to a timer circuit 220 and a communication line I/F 222. The I/O 210 is also connected to the facsimile communication control circuit (modem) 236 and the devices of the image reading unit 238 and the image forming unit 240.

The timer circuit 220 counts time as a trigger for switching the facsimile communication control circuit 236, the image reading unit 238, and the image forming unit 240 to a power-saving state (power non-supply state) (hereinafter, also referred to as a "system timer").

The main controller 200 and the devices (the facsimile communication control circuit 236, the image reading unit 238, and the image forming unit 240) are supplied power from the power supply device 202 (see the dotted line in FIG. 4). In FIG. 4, the power supply line is indicated by a single line (dotted line), but the power supply line actually includes two or three lines.

Power Supply Device

As shown in FIG. 4, the input power supply line 244 drawn from the commercial power source 242 is connected to a main switch 246. By turning on the main switch 246, the first power supply unit 248 and the second power supply unit 250 may be supplied with power. Although not shown in the drawing, the second power supply line 250 is branched from a line downstream from the main switch 246 and is wired to be supplied with power from the commercial power source 242.

The first power supply unit 248 includes a control power generating unit 248A, which is connected to a power supply control circuit 252 of the main controller 200. The power supply control circuit 252 supplies power to the main controller 200, is connected to the I/O 210, and performs a switching control of connecting or disconnecting the power supply lines to the devices (the facsimile communication control circuit 236, the image reading unit 238, and the image forming unit 240) in accordance with a control program of the main controller 200.

On the other hand, a first sub power supply switch 256 (hereinafter, also referred to as "SW-1") is installed in the power supply line 254 (ground side) connected to the second power supply unit 250. The ON and OFF of the SW-1 is controlled by the power supply control circuit 252. That is, when the SW-1 is turned off, the second power supply unit 250 does not operate (in a state where the power consumption is 0).

The second power supply unit 250 includes a 24V power supply unit 250H (LVPS2) and a 5V power supply unit 250L (LVPS1). The 24V power supply unit 250H (LVPS2) is a power source mainly used for a motor.

The 24V power supply unit 250H (LVPS2) and the 5V power supply unit 250L (LVPS1) of the second power supply unit 250 are selectively connected to an image reading unit power supply 258, an image forming unit power supply 260, a facsimile communication control circuit power supply 264, and a UI touch panel power supply 266.

The image reading unit power supply 258 uses the 24V power supply unit 250H (LVPS2) as an input source and is connected to the image reading unit 238 via a second sub power supply switch 268 (hereinafter, also referred to as "SW-2").

The image forming unit power supply 260 uses the 24V power supply unit 250H (LVPS2) and the 5V power supply unit 250L (LVPS1) as an input source and is connected to the image forming unit 240 via a third sub power supply switch 270 (hereinafter, also referred to as "SW-3").

The facsimile communication control circuit power supply 264 uses the 24V power supply unit 250H (LVPS2) and the 5V power supply unit 250L (LVPS1) as an input source and is connected to the facsimile communication control circuit 236 and the image forming unit 240 via a fourth sub power supply switch 274 (hereinafter, also referred to as "SW-4").

The UI touch panel power supply 266 uses the 5V power supply unit 250L (LVPS1) and the 24V power supply unit 250H (LVPS2) as an input source and is connected to the UI touch panel 216 (including the backlight unit 216BL) via a fifth sub power supply switch 276 (hereinafter, also referred to as "SW-5"). The original function (excluding the backlight unit 216BL) of the UI touch panel 216 may be supplied with power from a power-saving monitoring control unit 24.

The ON and OFF of the second sub power supply switch 268, the third sub power supply switch 270, the fourth sub power supply switch 274, and the fifth sub power supply switch 276 are controlled on the basis of a power supply selection signal from the power supply control circuit 252 of the main controller 200, similarly to the first sub power supply switch 256. Although not shown in the drawing, the switches or lines supplied with power from the 24V power supply unit 250H and the 5V power supply unit 250L are configured by two systems. The power supply switches 268 to 276 may be disposed in the devices as the power supply destinations instead of the power supply device 202.

In the above-mentioned configuration, since the devices (the facsimile communication control circuit 236, the image reading unit 238, and the image forming unit 240) are selectively supplied with power by functions and the devices unnecessary for an instructed function are not supplied with power, only the minimum necessary power may be supplied.

Monitoring Control for Changing Mode of Image Processing Apparatus

Here, the functions of the main controller 200 according to this exemplary embodiment may be partially stopped to achieve the minimum necessary power consumption. Alternatively, most of the power supply to the main controller 200 may be stopped. These cases may be collectively referred to as "sleep mode (power-saving mode)" (see FIG. 5).

The sleep mode may be started, for example, by starting up the system timer when an image process is ended. That is, the supply of power is stopped in a predetermined time after the system timer is started up. When a certain operation (such as a hardware key operation) is performed until the predetermined time passes, the counting of the timer for the sleep mode is stopped and the system timer is started up again when a next image process is ended.

On the other hand, in the sleep mode, a power-saving monitoring control unit 24 (see FIG. 4) as a device always supplied with power is connected to the I/O 210. The power-saving monitoring control unit 24 may include, for example, an IC chip which is called ASIC, which stores an operating program, and which has a CPU, a RAM, and a ROM operating in accordance with the operating program.

During the monitoring in the power-saving mode, it is on the premise that, for example, when a print request is transmitted from a communication line detecting unit or a FAX reception request is transmitted from a FAX line detecting unit, the power-saving monitoring control unit 24 supplies power to the devices in sleep (during power saving) by controlling the first sub power supply switch 256, the second sub power supply switch 268, the third power supply switch 270, the fourth sub power supply switch 274, and the fifth sub power supply switch 276 through the use of the power supply control circuit 252.

Control of Power Supply/Blocking of Main Controller

As shown in FIG. 4, a power saving control button 26 (simply also referred to as a "power saving button 26") is connected to the I/O 210 of the main controller 200. The power saving mode may be released by allowing a user to operate the power saving control button 26 during the power saving. The power saving control button 26 also has a function of forcibly blocking the supply of power to the corresponding unit and causing the unit to enter the power-saving mode by operating the power saving control button when power is supplied to the corresponding unit.

Here, for monitoring in the sleep mode, it is preferable that the power saving control button 26 or the detection units in addition to the power-saving monitoring control unit 24 be supplied with the minimum necessary power in the power saving mode. That is, even in the sleep mode in which the supply of power is blocked, the units may be supplied with power which is equal to or less than predetermined power (for example, equal to or less than 0.5 W) and which is necessary for determining whether the supply of power should be performed.

As a specific period in the sleep mode, a period of time in which the minimum necessary power is supplied mainly to the main controller 200 and the input system such as the UI touch panel 216 or an IC card reader 217 may be set. This is the result of consideration of user convenience. In this case, in order to guarantee the power saving in the UI touch panel 216, it is preferable that the backlight unit 216BL be turned off or the luminance thereof be lowered in comparison with the normal luminance.

The specific period is tentatively named an awake mode (awk) in FIG. 5, but this mode is not necessary.

Function of Motion Sensor

In the sleep mode, when a user stands in front of the image processing apparatus 10 and then operates the power saving control button 26 to restart the supply of power, time may be necessary until the image processing apparatus 10 is started up.

Accordingly, the power-saving monitoring control unit 24 is provided with a first motion sensor 28 and a second motion sensor 30. In the sleep mode, before a user presses the power saving release button, the user is detected with the motion sensors and the supply of power is early restarted to allow the user to rapidly use the image processing apparatus. The power saving control button 26, the first motion sensor 28, and the second motion sensor 30 are together used, but all the monitoring may be performed only by the use of the first motion sensor 28 and the second motion sensor 30.

As shown in FIG. 4, the first motion sensor 28 and the second motion sensor 30 include detection units 28A and 30A and circuit boards 28B and 30B. The circuit boards 28B and 30B adjust the sensitivity of signals detected by the detection units 28A and 30A or generates an output signal.

The first motion sensor 28 and the second motion sensor 30 use the word, "motion", which is a noun used in this exemplary embodiment, and mean that at least a person may be sensed (detected), in other words, that the motion sensing includes the sensing (detecting) of a moving object other than a person. Accordingly, in the following description, a detection target of a motion sensor may be mentioned as a "person", but a robot working instead of a person or the like is also in the monitoring target range. On the contrary, when a special sensor capable of sensing only a person is present, the special sensor may be used. Hereinafter, it is assumed that a moving object, a person, a user, and the like are treated as having the same meaning as a target detected by the first motion sensor 28 and the second motion sensor 30 and are distinguished if necessary.

"First Motion Sensor"

The specification of the first motion sensor 28 according to this exemplary embodiment includes detecting the motion of a moving object around the image processing apparatus 10 (for example, in the range of 1 m to 5 m). In this case, an infrared sensor using the pyroelectric effect of a pyroelectric element may be representatively used (pyroelectric sensor). In this exemplary embodiment, a pyroelectric sensor is used as the first motion sensor 28.

The sensor using the pyroelectric effect of a pyroelectric element which is used as the first motion sensor 28 is characterized most in that the detection area is wide. Since the motion of a moving object is sensed, the presence of a person stopping in the detection area is not detected. For example, when a high-level signal is output with the movement of a person and the person in the detection area stops, the signal is changed to a low-level signal.

The "stop" in this exemplary embodiment includes the perfect stop as in a still image captured with a still camera and also includes a person's stopping in front of the image processing apparatus 10 to operate the image processing apparatus. Accordingly, small motions (motions based on breathing) in a predetermined range and motions of hands, feet, neck, and the like are in the range of the stopping.

However, when a person stretches in the place while the person waits for the processes such as image forming or image reading in front of the image processing apparatus 10, the motion sensor 28 may detect the presence of the person.

Therefore, instead of defining the "stopping" and setting a threshold for detecting a motion by the use of the first motion sensor 28, the threshold value may be set relatively wide and standard and may depend on the detection state of the first motion sensor 28 based on environments (temperature, humidity, and the like). That is, the threshold may be set experimentally or statistically in the place where the apparatus is installed so that it represents that a person moves when the first motion sensor 28 outputs one (for example, a high-level signal) out of binary signals, and a person stops when the person is present in the detection area of the first motion sensor 28 and the other (for example, a low-level signal) out of binary signals is output.

The specification of the first motion sensor 28 according to this exemplary embodiment includes detecting the motion of a moving object around the image processing apparatus 10 (for example, in the range of 0 m to 5 m).

"Second Motion Sensor"

On the other hand, the specification of the second motion sensor 30 according to this exemplary embodiment includes detecting the presence (presence or absence) of a moving object. A reflective sensor having a light-emitting portion and a light-receiving portion may be representatively used as the sensor applied to the second motion sensor 30 (reflective sensor). The light-emitting portion and the light-receiving portion may be separated.

The reflective sensor used as the second motion sensor 30 is characterized most in that the presence of a moving object may be satisfactorily detected on the basis of the information on whether light incident on the light-receiving portion is blocked/non-blocked. Since the light intensity incident on the light-receiving portion is associated with the light intensity emitted from the light-emitting portion, the detection area is relatively narrow.

The first motion sensor 28 is not limited to the pyroelectric sensor and as the second motion sensor 30 is not limited to the reflective sensor, as long as they may achieve the following functions as the first motion sensor 28 and the second motion sensor 30.

In this exemplary embodiment, the maximum detection areas (for example, a first area F and a second area N in FIGS. 6 and 7) of the first motion sensor 28 and the second motion sensor 30 are set.

Figure 6:
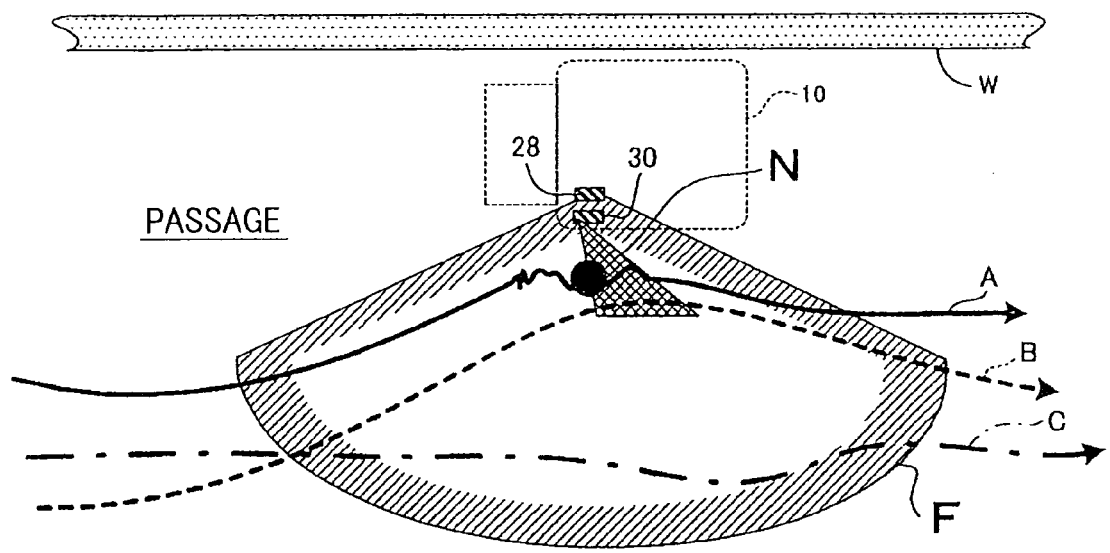
FIG. 6 is a plan view illustrating the image processing apparatus and the periphery thereof according to the exemplary embodiment.

The first area F (also simply referred to as "area F") which is shown in FIG. 6 and which is a relatively-distant detection area is the detection area of the first motion sensor 28, which serves as a sensor detecting a relatively-remote moving object. The second area N (also simply referred to as "area N") which is shown in FIG. 6 and which is a relatively-near detection area is the detection area of the second motion sensor 30, which serves as a sensor detecting a relatively-close moving object.

The detection area (see the first area F in FIG. 6) of the first motion sensor 28 depends on the environments of the place where the image processing apparatus 10 is installed, but the threshold point (the farthest position) as a reference is preferably in the range of 0.8 to 3 m. On the other hand, the detection area (see the second area N in FIG. 6) of the second motion sensor 30 means a range in which the UI touch panel 216 or the hardware key of the image processing apparatus 10 may be operated and the threshold point (the farthest position) as a reference is preferably in the range of 0.2 to 1.0 m. The threshold point of the first motion sensor 28 is farther than the threshold point of the second motion sensor 30 after both threshold points are set.

Trace A shows a trace in which a person approaches the operable position for the image processing apparatus, stops to operate the image processing apparatus, and goes away. Thus, the traversed order of areas is: out of area, area F, area N, and out of area.

Trace B shows a trace in which a person approaches and passes through the operable position for the image processing apparatus. Thus, the traversed order of areas is: out of area, area F, area N, area F, and out of area.

Trace C shows a trace in which a person does not approach the operable position for the image processing apparatus and passes the vicinity thereof. Thus, the traversed order of areas is: out of area, area F, and out of area.

In the reflective sensor applied for the second motion sensor 30, it is possible to easily adjust the sensitivity by adjusting the resistance of internal electric components. On the contrary, in the pyroelectric sensor applied for the first motion sensor 28, it is difficult to adjust the detection distance.

Since the threshold point in the specification of the first motion sensor 28 (the pyroelectric sensor) is 5 m, it is necessary to adjust the threshold point to 0.8 to 3 m.

Therefore, in this exemplary embodiment, a desired detection distance (threshold point) may be achieved on the basis of the installation position of the first motion sensor 28 and the peripheral structure thereof.

First Motion Sensor and Peripheral Configuration

Figure 7:
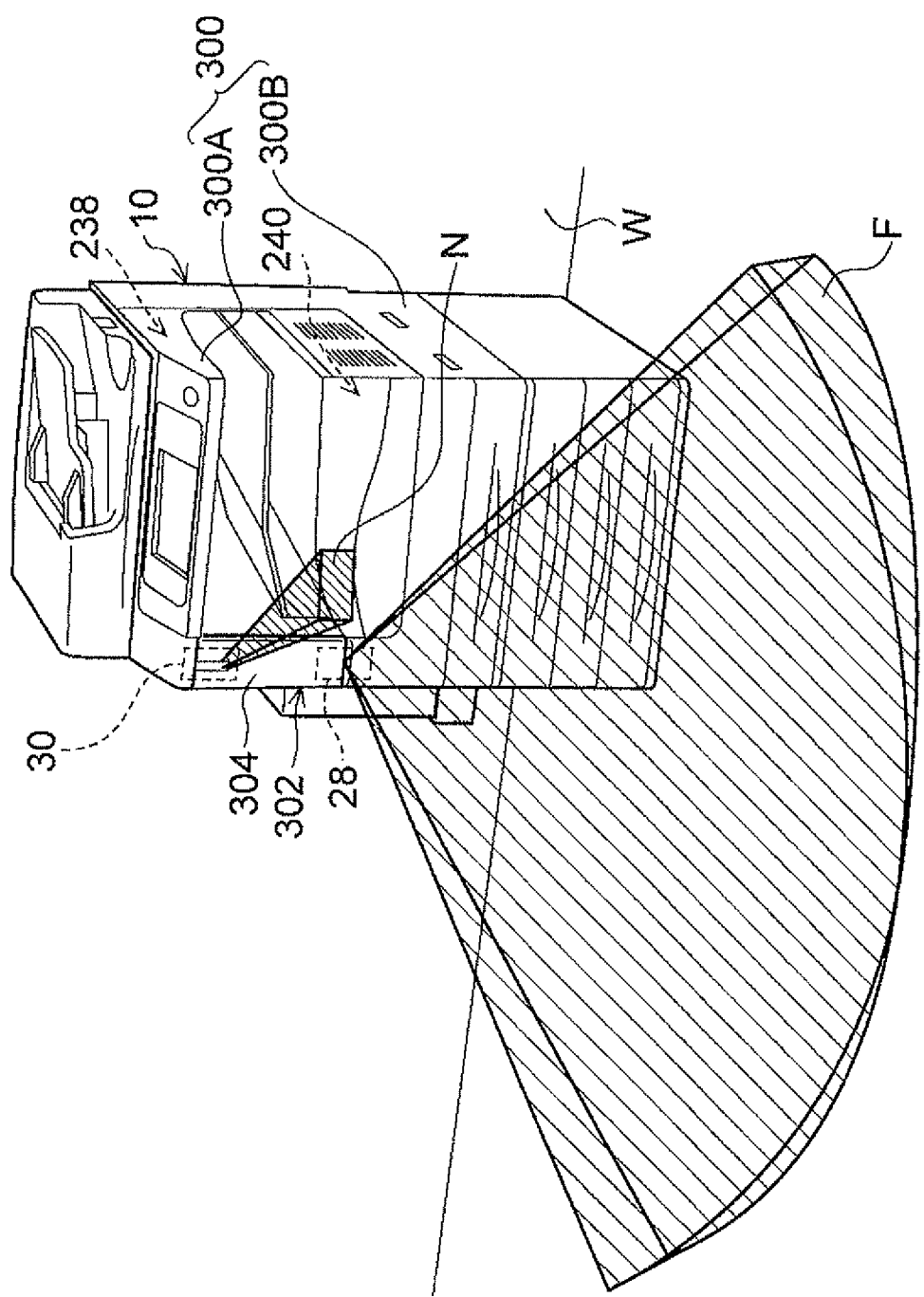
FIG. 7 is a perspective view illustrating the image processing apparatus and the periphery thereof according to the exemplary embodiment.

As shown in FIG. 7, in the image processing apparatus 10, an image reading device 238 and an image forming device 240 are covered with a chassis 300 and the first motion sensor 28 (including the second motion sensor 30) is attached to a vertically-long rectangular pillar portion 302 in the chassis 300. The pillar portion 302 is a portion connecting an upper chassis 302A covering the image reading device 238 and a lower chassis 302B covering the image forming device 240 and a recording sheet transporting system or the like is assembled into the pillar portion.

Figure 8:
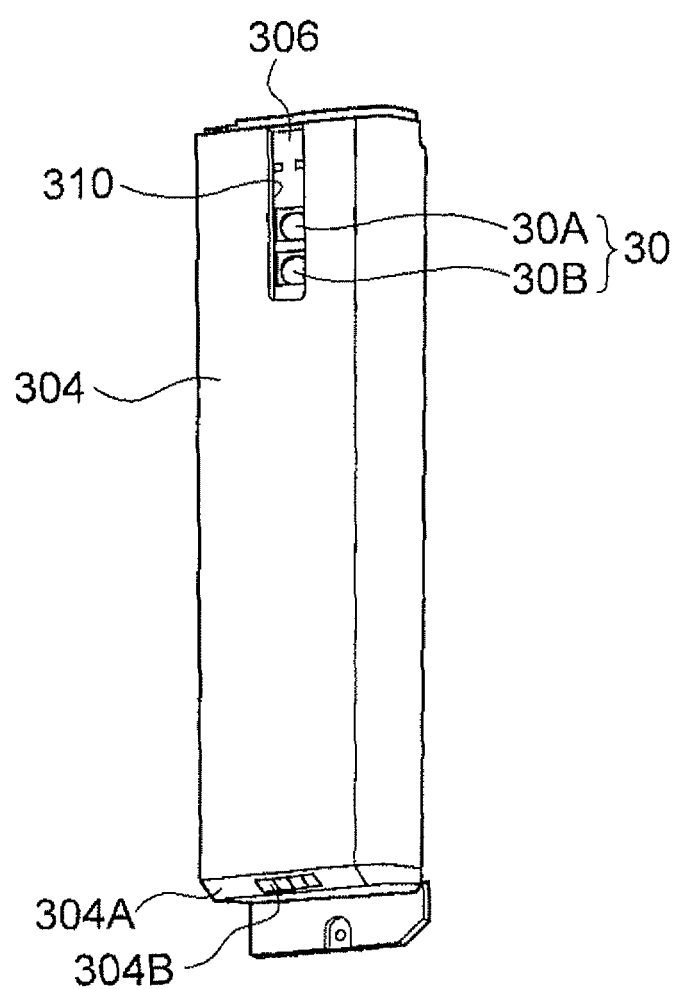
FIG. 8 is a perspective view illustrating a cover member formed on the front surface of a pillar portion according to the exemplary embodiment.

A vertically-long rectangular cover member 304 covering the pillar portion 302 with a design factor is attached to the front surface of the pillar portion 302. As shown in FIG. 8, a sensor unit 306 is disposed on the rear surface of the cover member 304. The sensor unit 306 includes a sensor-assembling structure 308 (see FIG. 9) to which the first motion sensor 28 and the second motion sensor 30 are attached.

A vertically-long slit 310 is formed at the upper end of the cover member 304 in FIG. 8, and the light-receiving portion 30A and the light-emitting portion 30B of the second motion sensor 30 are disposed on the rear surface of the slit 310. Although not shown in the drawings, a concealment member having relatively lower transmittance (transmittance of 50% or less) is inserted into the slit 310. The concealment member is provided to conceal the second motion sensor 30 from the outside and to guarantee the above-mentioned design factor, and the detection function of the second motion sensor 30 is basically maintained.

Figure 9:
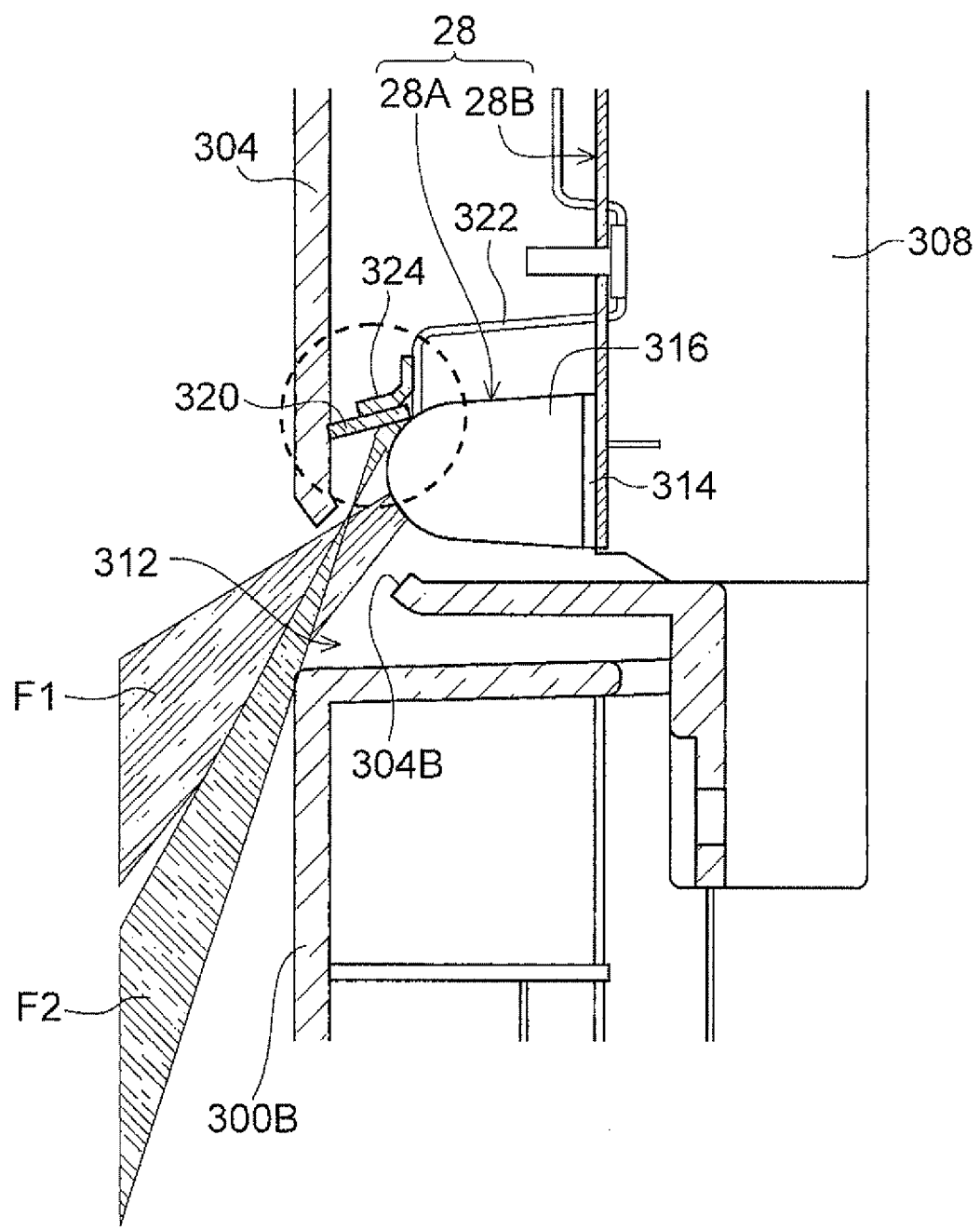
FIG. 9 is a side cross-sectional view illustrating the internal structure of the pillar portion according to the exemplary embodiment.

As shown in FIG. 9, a space 312 is formed between the bottom of the cover member 304 and the top of the lower chassis 300B. The lower end of the cover member 304 in FIG. 9 has a so-called chamfered shape (a chamfered portion 304A) and the opening area of the space 312 is larger than the gap size on the deep side.

A rectangular through-hole 304B is formed in the chamfered portion 304A and the first motion sensor 28 is attached to the lower end of the structure 308. Accordingly, the through-hole 304B serves as a monitoring window for detecting a moving object through the use of the first motion sensor 28. Here, the through-hole 304B is also referred to as a monitoring window 304B.

Since the monitoring window 304B is formed in the chamfered portion 304A, it is less visible from the front side of the apparatus, compared with the case where it is formed on the front surface, thereby not damaging the design factor of the cover member 304.

On the other hand, the first motion sensor 28 includes the detection unit 28A and the circuit board 28B and the circuit board 28B is attached to the structure 308 disposed to be parallel to the cover member 304. Accordingly, the detection unit 28A does not face the chamfered portion 304A and the central axis is directed from the front surface (the rear surface) of the cover member 304.

Figure 10A:
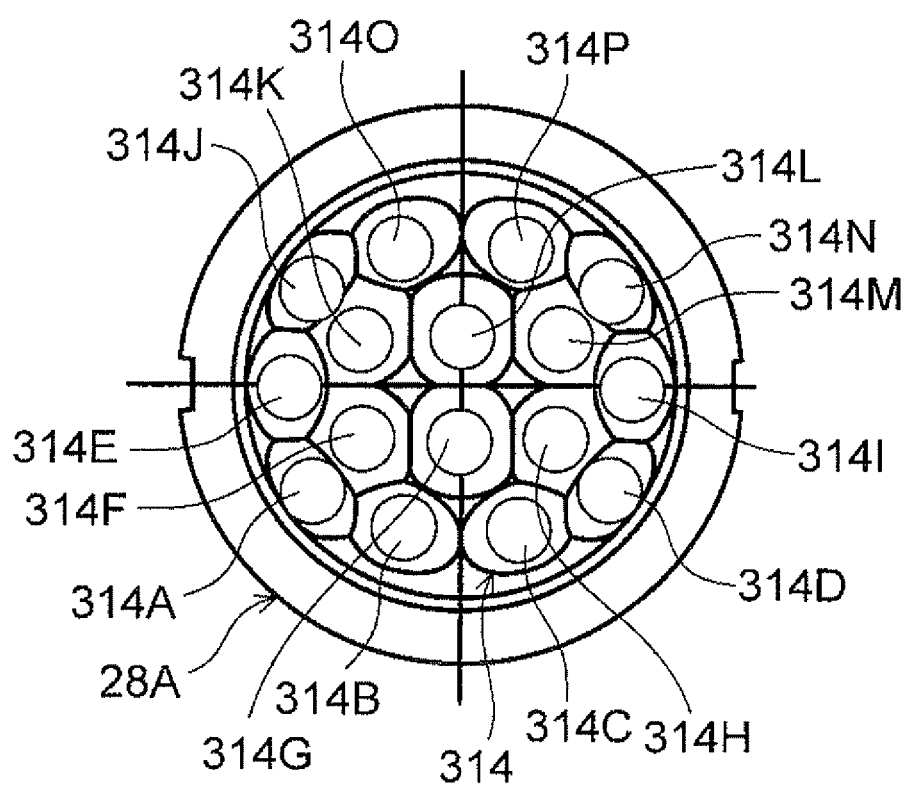
FIGS. 10A and 10B are front views illustrating a sensor unit of a first motion sensor according to the exemplary embodiment, where

FIG. 10A is a front view of the detection surface of the detection unit 28A of the first motion sensor 28 (pyroelectric sensor) according to this exemplary embodiment, where the detection unit 28A is a set of plural detection elements (a set of 16 detection elements 314A, 314B, 314C, 314D, 314E, 314F, 314G, 314H, 314I, 314J, 314K, 314L, 314 M, 314N, 314O, and 314P in this exemplary embodiment). The detection elements are collectively referred to as detection elements 314.

The detection elements 314 may detect infrared rays, the variations in infrared rays input to the detection elements 314 are combined into an electric signal and output as an electric signal of a single sensor by the circuit board 28B.

The detection unit 28A is covered with a bullet-like (a cylindrical shape of which the tip has a semi-spherical shape) lens cover 316 (see FIG. 9). Lens portions 318A to 318P (see FIG. 10B, which are collectively referred as "lens portions 318") partitioned depending on the number of detection elements 314 (16 in this exemplary embodiment) are formed on the semi-sphere-like surface of the tip of the lens cover 316. Accordingly, the area focused by each lens portion 318 is the detection area of the corresponding detection element 314. At least the primary areas (detection areas in the specification) of the detection areas constitute the same area. Accordingly, as more detection elements 314 are effectively used, the intensity (accuracy) of the electric signal to be output becomes higher.

Figure 10B:
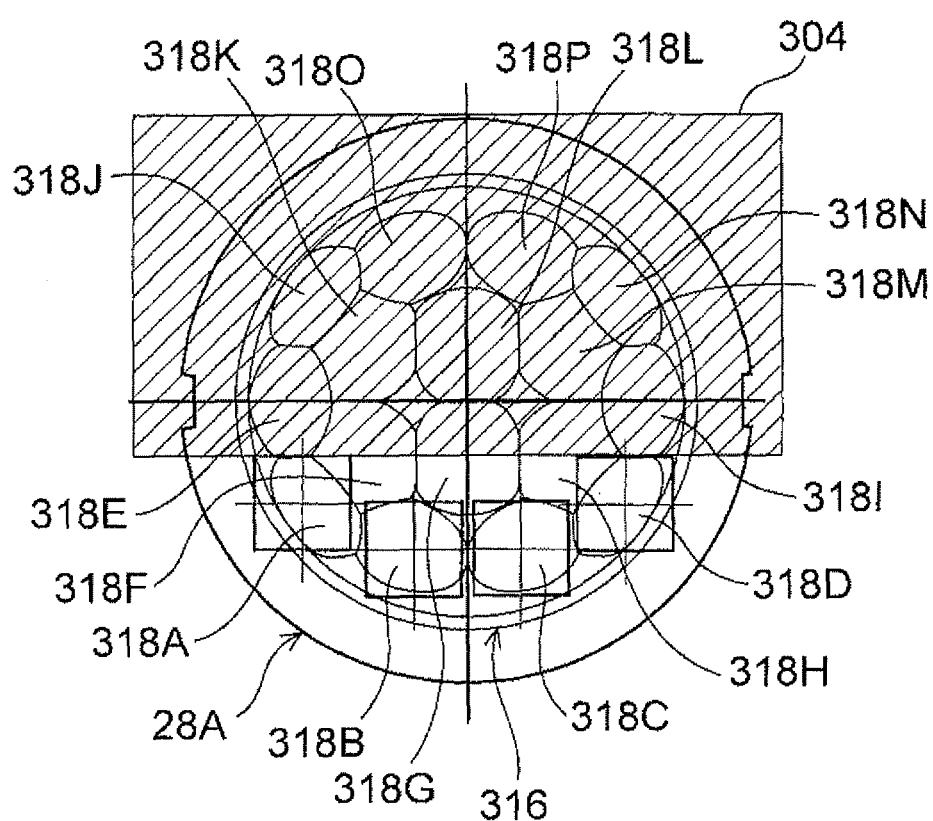

As shown in FIGS. 9 and 10B, the front surface of the first motion sensor 28 is partitioned into the backside of the front surface of the cover member 304 (see the hatched portion in FIG. 10B) and the monitoring window 304B formed in the chamfered portion 304A. In this state, some detection elements 314 (the detection elements 314A to 314D occupying about ⅓ in the lower part in FIG. 10B) are effective detection elements 314A to 314D capable of detecting infrared rays from the monitoring window 304B and the other detection elements are ineffective detection elements 314E to 314P not capable of detecting infrared rays.

Therefore, in this exemplary embodiment, as shown in FIG. 9, a reflecting mirror 320 (optical member) is disposed at a position opposite to the optical axes of the ineffective detection elements 314E to 314P to deflect the optical axes so as to pass through the monitoring window 304B.

The "deflection" includes reflecting the optical axes with the reflecting mirror 320 and refracting the optical axes with a lens, a prism, or the like, but is different from the "polarization" of axially rotating the optical axes.

That is, as shown in FIG. 9, a leaf spring 322 keeping the position of the first motion sensor 28 is formed in the circuit board 28B. The tip of the leaf spring 322 comes in contact with the lens cover 316 to prevent the positional displacement of the lens cover 316, for example, due to the vibration during operation of the apparatus.

In this way, since the leaf spring 322 has such rigidity enough to maintain the first motion sensor 28, the leaf spring 322 is used as a support to attach the reflecting mirror 320 to the tip of the leaf spring 322 with an L-shaped bracket 324 interposed therebetween.

The structure supporting the reflecting mirror 320 is not limited to the leaf spring 322, but the reflecting mirror 320 may be disposed on the rear side of the cover member 304 or a support may be made to extend from the structure 308, as long as the reflecting mirror 320 faces the optical axes of the ineffective detection elements 314E to 314P of the first motion sensor 28. Uneven patterns may be formed on the rear side of the cover member 304 by molding and a reflecting mirror surface may be formed through the use of a chemical process such as a plating process (a chromium-plating process or the like).

Since the optical axes of the ineffective detection elements 314E to 314P shown in FIG. 10B are deflected by the reflecting mirror 320 to pass through the monitoring window 304B due to the addition of the reflecting mirror, the ineffective detection elements may be used as effective detection elements and the detection area F1 of the original effective detection elements 314A to 314D is interpolated by the area F2. That is, the optical axes of the effective detection elements 314A to 314D serve as reference optical axes and the optical axes of the ineffective detection elements 314E to 314P serve as interpolation axes.

In FIG. 9, the detection area F1 of the original effective detection elements 314A to 314D and the detection area F2 of the ineffective detection elements 314E to 314P which newly become effective are different from each other. In this case, the purpose of the interpolation is an "increase in detection area". This depends on the angle of the reflecting mirror 320. For example, when the angle of the reflecting mirror 320 is adjusted to overlap the detection area F2 of the ineffective detection elements 314E to 314P which newly become effective with the detection area F1 of the original effective detection elements 314A to 314D, the purpose of the interpolation is an "increase in detection intensity". Therefore, the purpose of the interpolation may be selected depending on the specification.

When the increase in detection area is selected as the purpose of the interpolation, the detection optical axis of the first motion sensor 28 is directed to the downside (to the bottom). Accordingly, the initial detection target is only a user's feet, but as the user approaches the apparatus, the detection target is widened from the feet to the waist, whereby the "increase in detection intensity" is also achieved secondarily.

Control of Power Supply to Sensor

In this exemplary embodiment, the second motion sensor 30 is not always supplied with power. The second motion sensor 30 is supplied with power to start up its operation when a moving object (user) enters the first area F of FIG. 6 monitored by the first motion sensor 28, and is then instructed to start up from the sleep mode to the standby mode when the moving object (user) enters the second area N of FIG. 6 monitored by the second motion sensor 30.

That is, the minimum necessary power is supplied in cooperation with two motion sensors (the first motion sensor 28 and the second motion sensor 30) having different detection areas.

On the other hand, the function of the timer formed in the power-saving monitoring control unit 24 is used along with the state where the first motion sensor 28 detects a moving object to block the supply of power to the second motion sensor 30. This function of the timer is also referred to as a "sensor timer" to distinguish it from the system timer.

The sensor timer is one function of the power-saving monitoring control unit 24. That is, since the control system includes an operation clock, the timer may be generated from the clock signal or a counter program counting the time every predetermined time for each process may be prepared.

As shown in FIG. 6, the relation between a moving object (user) and the image processing apparatus 10 is substantially classified into three patterns. A first pattern is a pattern in which a person approaches an operable position of the image processing apparatus 10 for the purpose of use (see the movement (pattern A) indicated by the arrow A in FIG. 6). A second pattern is a pattern in which a person approaches an operable position of the image processing apparatus for the purpose other than use (see the movement (pattern B) indicated by the arrow B in FIG. 6). A third pattern is a pattern in which a person does not approach the operable position of the image processing apparatus but goes to a position corresponding to a distance by which this pattern is changed to the first pattern or the second pattern (see the movement (pattern C) indicated by the arrow C in FIG. 6).

In this exemplary embodiment, the time of permitting the supply of power to the second motion sensor 30 and the time of blocking the supply of power to the second motion sensor 30 based on the movements (a person's movement based on patterns A to C shown in FIG. 6) are controlled on the basis of the detection information from the first motion sensor 28 or the detection information from the first motion sensor 28 and the counting information of the sensor timer.

The operation in this exemplary embodiment will be described below.

Change of Mode in Controlling Power Supply of Image Processing Apparatus (Device)

The modes and events serving as a trigger of changing the mode in the image processing apparatus 10 will be described with reference to the timing diagram shown in FIG. 5.

The operation state of the image processing apparatus 10 when not performing any process is in the sleep mode. In the sleep mode, power is supplied to only the power-saving monitoring control unit 24 in this exemplary embodiment.

Here, when a startup trigger (the detection of a moving object through the first motion sensor 28 and the second motion sensor 30 or the operation of the power saving control button 26 or the like) is given, the operation state is changed to the warm-up mode.

Here, the second motion sensor 30 is not supplied with power in the sleep mode and is gradually supplied with power in response to the detection of a moving object through the first motion sensor 28. Since a moving object detected by the second motion sensor 30 is more possibly a user using the apparatus than the moving object detected by the first motion sensor 28, the detection of a moving object by the second motion sensor is an appropriate power supply time to the main controller 200.

After this startup trigger, the operation state is defined as being still in the sleep mode and only the UI touch panel 216 may be started up on the premise of the supply of power to the main controller 200. Alternatively, since the amount of power supply is larger than that in the supply of power to only the power-saving monitoring control unit 24 due to the startup of the main controller 200 and the UI touch panel 216, this operation state may be provisionally defined as an awake mode "awk" (awk) (wake-up mode) (see the parenthesis [ ] in the sleep mode in FIG. 5). When an operational input (key input) to the UI touch panel 216 or the like is given in this awake mode, the operation state is changed to the warm-up mode.

The startup trigger is mainly a signal or information based on the detection result of the second motion sensor 30, but an operator's operation of releasing a power saving mode may be used as the startup trigger.

In the warm-up mode, since the image processing apparatus 10 is rapidly changed to a workable state, the maximum power is consumed out of all the modes. For example, it is known that when an IH heater is used as a heater of the fixing unit, the warm-up mode time is shorter than that in the case where a halogen lamp is used as a heater.

When a warming-up operation in the warm-up mode is ended, the image processing apparatus 10 is changed to the standby mode.

The standby mode is literally a mode in which "it is ready to perform an operation". In this state, the image processing apparatus 10 may perform an image processing operation at once.

Accordingly, when a job executing operation is given by a key input, the operation state of the image processing apparatus 10 is changed to a running mode and performs an image process based on the instructed job.

When the image process is ended (when all the continuous jobs on standby are ended), the operation state of the image processing apparatus 10 is changed to a standby mode in response to a standby trigger. The system timer may start counting the time after performing the image process and the standby trigger may be output after a predetermined time passes, thereby changing the operation state to the standby mode.

When a job executing instruction is given in the standby mode, the operation mode is changed again to the running mode. The operation state is changed to the sleep mode when an end trigger is detected or a predetermined time passes.

The end trigger is, for example, a signal or information based on the detection result of the second motion sensor 30. The system timer may be used together.

All the changes of the modes in the actual operation of the image processing apparatus 10 are not performed in time series in accordance with this timing diagram. For example, the processes may be stopped in the standby mode after the warm-up mode and the operation state may be changed to the sleep mode.

Here, the devices operating with the supply of power may perform their processes, since the operation state is changed from the sleep mode in FIG. 5 to the standby mode via the awake mode and the warm-up mode.

In this way, the image processing apparatus 10 according to this exemplary embodiment is switched between the modes and the amount of power supply varies depending on the modes.

Monitoring of First Motion Sensor in Sleep Mode

Here, in this exemplary embodiment, in the sleep mode, only the first motion sensor 28 is basically supplied with power and monitors an approach state of a moving object. The monitoring area (detection area) corresponds to the area F in FIG. 6 and the presence of a moving object is detected by analyzing (the variation of) an electric signal based on infrared rays input to the detection unit 28A (the plural detection elements 314) of the first motion sensor 28.

At this time, when the overall detection surface (for example, the lens cover 316) of the first motion sensor 28 is exposed, all the detection elements 314 may be effectively used, but the cover member 316 having a high design factor is structurally disposed on the rear side.

In order to restrict the detection distance to 0.8 to 3 m, it is necessary to block the upper part (about ⅔) of the detection elements 314 with (the rear side of) the cover member 316 and to allow only the optical axes of some detection elements 314 (the effective detection elements 314A to 314D) to pass through the monitoring window 304B formed in the chamfered portion 304A. Accordingly, there is no means for externally inputting infrared rays to the ineffective detection elements 314E to 314P and the detection intensity of the first motion sensor 28 as a whole decreases (theoretically, about ⅓ of the detection intensity). The decrease in detection intensity adversely affects the detection accuracy.

Therefore, in this exemplary embodiment, the reflecting mirror 320 is formed to face the optical axes of the ineffective detection elements 314E to 314P, as shown in FIG. 9.

The optical axes (deflected optical axes) reflected by the reflecting mirror 320 pass through the monitoring window. In other words, the ineffective detection elements 314E to 314P are ineffective detection elements 314E to 314P which newly become effective in addition to the original effective detection elements 314A to 314D.

Here, as shown in FIG. 9, the detection area of the original effective detection elements 314A to 314D is considered to be separated 0.5 m from the threshold point (the maximum detection distance, for example, 0.8 m) and the detection area of the ineffective detection elements 314E to 314P is considered to be separated 0.5 m to 0.3 m.

In this case, since the detection areas do not overlap with each other, the purpose of the interpolation is mainly the "increase in detection area". The detection axis of the first motion sensor 28 is directed to the downside (to the bottom). Accordingly, the initial detection target is only a user's feet, but as the user approaches the apparatus, the detection target is widened from the feet to the waist, whereby the "increase in detection intensity" is also achieved secondarily.

By dividing the detection area into two areas, for example, the distant area (the original effective detection elements 314A to 314D) may be used to mainly monitor a moving object approaching from the front side and the close area (the ineffective detection elements 314E to 314P which newly become effective) may be used mainly monitor a moving object approaching from the lateral side.

MODIFIED EXAMPLE 1

Figure 11:
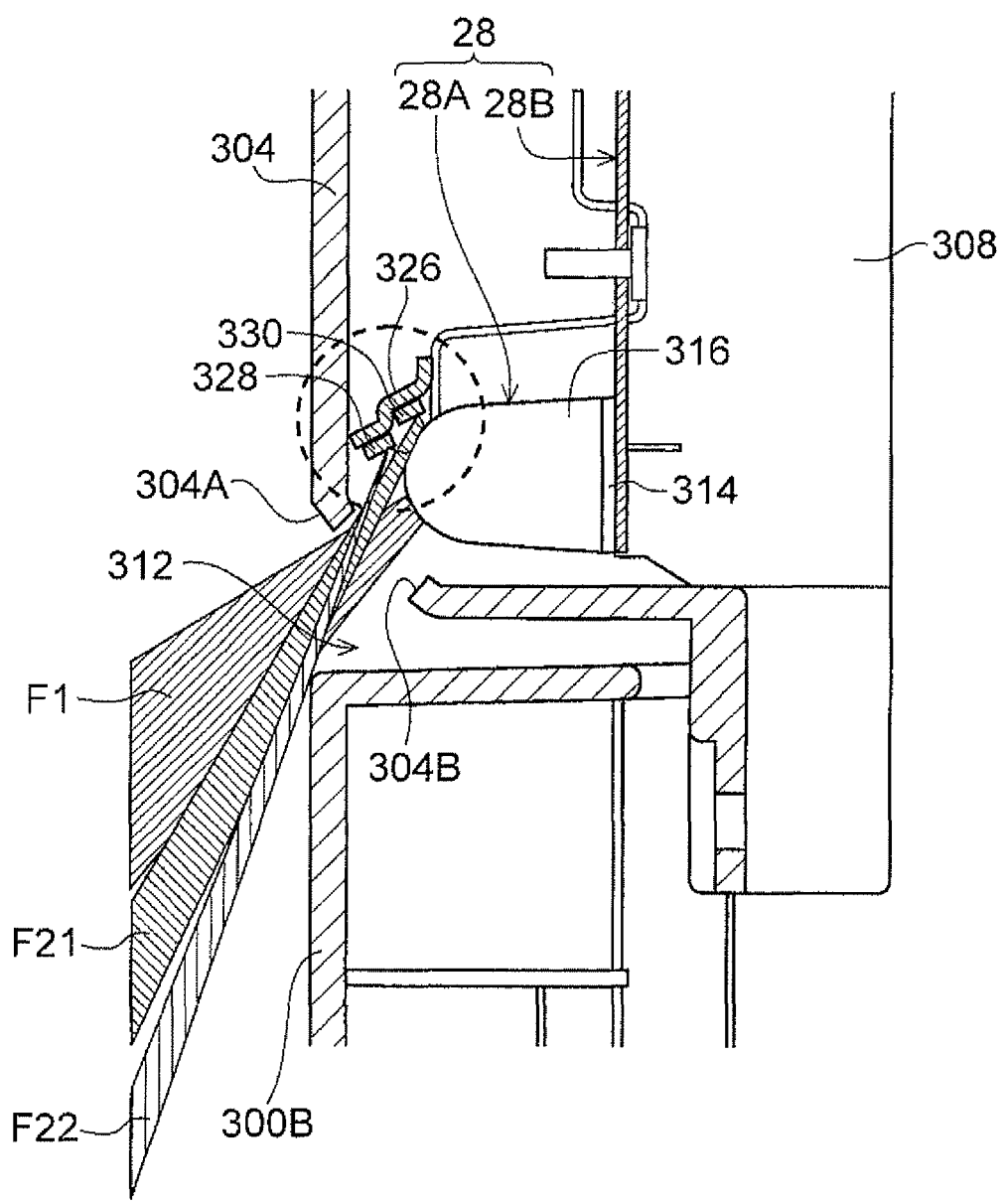
FIG. 11 is a side cross-sectional view illustrating the internal structure of a pillar portion according to Modified Example 1.

In this exemplary embodiment, as shown in FIG. 9, the single reflecting mirror 320 faces all the ineffective detection elements 314E to 314P to reflect the optical axes and to pass through the monitoring window 304B. However, as shown in FIG. 11, two reflecting mirrors 328 and 330 may be attached with a bracket 326 having a step in the thickness direction. In this case, the ineffective detection elements 314E to 314P are divided into two parts and the optical axes are reflected at different reflection angles through the use of two reflecting mirrors 328 and 330. In this case, detection areas F21 and F22 are set as the detection area of the ineffective detection elements 314E to 314P which newly become effective in addition to the detection area F1 of the original effective detection elements 314A to 314D, and the purpose of the interpolation may be selectively set to the "increase in detection area" or the "increase in detection intensity".

MODIFIED EXAMPLE 2

Figure 12:
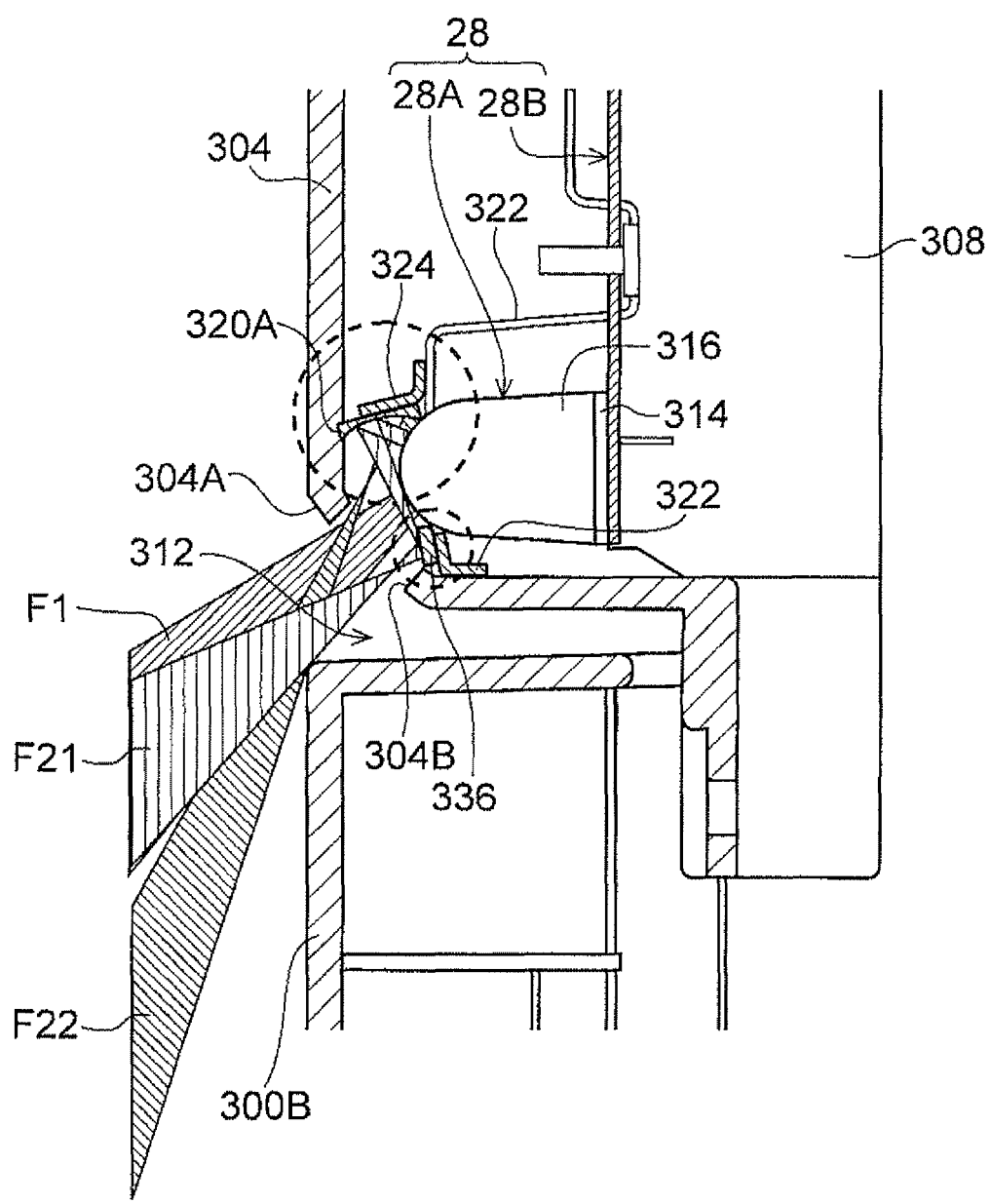
FIG. 12 is a side cross-sectional view illustrating the internal structure of a pillar portion according to Modified Example 2.

In this exemplary embodiment, as shown in FIG. 9, the single reflecting mirror 320 faces all the ineffective detection elements 314E to 314P to reflect the optical axes and to pass through the monitoring window 304B. However, as shown in FIG. 12, a concave reflecting mirror 320A (regardless of a spherical surface or an aspheric surface) may be used instead of the reflecting mirror 320 and a reflecting mirror 330 further reflecting the optical axes may be formed to face the optical axes reflected by the concave reflecting mirror. A triangular or saw-teethed reflecting mirror of which the reflecting surfaces have different angles may be used instead of the concave reflecting mirror 320A.

The additional reflecting mirror 330 is attached to the inside of the bottom surface of the cover member 304 with a bracket 332 interposed therebetween. By the two-stepped reflecting structure, an area F21 overlapping with the detection area of the original effective detection elements 314A to 314D and an area F2 increasing the detection area are formed as the detection area of the ineffective detection elements 314E to 314P which newly become effective and the purpose of the interpolation is "the increase in detection area+the increase in detection intensity".

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A moving object detecting device comprising:
   a detecting device body that includes a detection unit formed in a chassis covering the inside of an apparatus and disposed to correspond to a monitoring window of which at least an aperture area or an aperture size is restricted and which monitors a moving object approaching the apparatus and a circuit board unit controlling a signal output from the detection unit and that is disposed so that some optical axes among optical axes having detection surfaces of a plurality of infrared detecting elements, which are included in the detection unit, as focal points pass through the monitoring window and the other optical axes are blocked by the chassis; and
   an optical member that is formed in an inner wall of the chassis and that deflects the other optical axes of the infrared detection elements to pass through the monitoring window, wherein:
   the some optical axes among the optical axes of the infrared detection elements passing through the monitoring window are reference optical axes which are directed to the front side of the apparatus and the floor having the apparatus installed thereon to set a detection distance and a detection area of the detecting device body, and
   the other optical axes are interpolation optical axes used to interpolate the detection distance or the detection area based on the reference optical axes.

2. The moving object detecting device according to claim 1, wherein the detection unit is a pyroelectric sensor including:
   a plurality of detection elements that are two-dimensionally arranged on a main surface of the circuit board unit, to which infrared rays are input along respective optical axes, and that convert a variation in wavelength of the input infrared rays into an electric signal; and
   a lens cover that is disposed to cover the plurality of detection elements and that has an optical function of setting an optical axis of an infrared ray incident from a specific detection point as a focal position of each detection element, and
   wherein the intensity of the electric signal corresponding to the sensitivity for monitoring the moving object is proportional to the number of detection elements detecting the infrared rays.

3. A power supply control device comprising:
   a switching unit that switches a passive operation unit operating with a supply of power from a power source unit to any one of a power supply state where power is supplied to the passive operation unit and a power non-supply state where the supply of power is blocked;
   a chassis that covers the inside of an apparatus and that has a monitoring window of which at least an aperture area or an aperture size is restricted and which is used to monitor a moving object approaching the apparatus;
   a moving object detecting device including
      a detecting device body that includes a detection unit disposed to face the inner wall of the chassis and a circuit board unit controlling a signal output from the detection unit and that is disposed so that some optical axes among optical axes having detection surfaces of a plurality of infrared detecting elements, which is included in the detection unit, as focal points pass through the monitoring window and the other optical axes are blocked by the chassis, and
      an optical member that is formed in the inner wall of the chassis and that deflects the other optical axes of the infrared detection elements to pass through the monitoring window; and
   a return control unit that controls the switching unit to return the passive operation unit to the power supply state when the moving object detecting unit detects the moving object and a predetermined condition is satisfied in the power non-supply state.

4. The power supply control device according to claim 3, wherein
   the some optical axes among the optical axes of the infrared detection elements passing through the monitoring window are reference optical axes which are directed to the front side of the apparatus and the floor having the apparatus installed thereon to set a detection distance and a detection area of the detecting device body, and
   the other optical axes are interpolation optical axes used to interpolate the detection distance or the detection area based on the reference optical axes.

5. The power supply control device according to claim 4, wherein the detection unit is a pyroelectric sensor including:
   a plurality of detection elements that are two-dimensionally arranged on a main surface of the circuit board unit, to which infrared rays are input along respective optical axes, and that convert a variation in wavelength of the input infrared rays into an electric signal; and
   a lens cover that is disposed to cover the plurality of detection elements and that has an optical function of setting an optical axis of an infrared ray incident from a specific detection point as a focal position of each detection element, and
   wherein the intensity of the electric signal corresponding to the sensitivity for monitoring the moving object is proportional to the number of detection elements detecting the infrared rays.

6. The power supply control device according to claim 5, wherein the predetermined condition is satisfied when the detection by the moving object detecting device is defined as a first detection and a second detection is performed which is started with the first detection and which serves to detect the moving object at a position closer to the apparatus than at least the detection area of the first detection.

7. The power supply control device according to claim 4, wherein the predetermined condition is satisfied when the detection by the moving object detecting device is defined as a first detection and a second detection is performed which is started with the first detection and which serves to detect the moving object at a position closer to the apparatus than at least the detection area of the first detection.

8. The power supply control device according to claim 3, wherein the detection unit is a pyroelectric sensor including:
a plurality of detection elements that are two-dimensionally arranged on a main surface of the circuit board unit, to which infrared rays are input along respective optical axes, and that convert a variation in wavelength of the input infrared rays into an electric signal; and
a lens cover that is disposed to cover the plurality of detection elements and that has an optical function of setting an optical axis of an infrared ray incident from a specific detection point as a focal position of each detection element, and
wherein the intensity of the electric signal corresponding to the sensitivity for monitoring the moving object is proportional to the number of detection elements detecting the infrared rays.

9. The power supply control device according to claim 8, wherein the predetermined condition is satisfied when the detection by the moving object detecting device is defined as a first detection and a second detection is performed which is started with the first detection and which serves to detect the moving object at a position closer to the apparatus than at least the detection area of the first detection.

10. The power supply control device according to claim 3, wherein the predetermined condition is satisfied when the detection by the moving object detecting device is defined as a first detection and a second detection is performed which is started with the first detection and which serves to detect the moving object at a position closer to the apparatus than at least the detection area of the first detection.

11. An image processing apparatus comprising:
the power supply control device according to claim 5; and
as the passive operation unit at least one of an image reading unit reading an image from an original image, an image forming unit forming an image on a recording sheet on the basis of image information, a facsimile communication control unit transmitting an image to a destination under a predetermined communication procedure, a user interface unit receiving information from a user and informing the user of information, and a user identification unit identifying the user,
wherein an image process is performed in cooperation on the basis of an instruction from the user, and
wherein the monitoring window is disposed with respect to the installation position of the user interface unit or the user identification unit.

12. A moving object detecting device comprising:
a detecting device body that includes a detection unit formed in a chassis covering the inside of an apparatus and disposed to correspond to a monitoring window of which at least an aperture area or an aperture size is restricted and which monitors a moving object approaching the apparatus and a circuit board unit controlling a signal output from the detection unit and that is disposed so that some optical axes among optical axes having detection surfaces of a plurality of infrared detecting elements, which are included in the detection unit, as focal points pass through the monitoring window and the other optical axes are blocked by the chassis; and
an optical member that is formed in an inner wall of the chassis and that deflects the other optical axes of the infrared detection elements to pass through the monitoring window, wherein the detection unit is a pyroelectric sensor including:
a plurality of detection elements that are two-dimensionally arranged on a main surface of the circuit board unit, to which infrared rays are input along respective optical axes, and that convert a variation in wavelength of the input infrared rays into an electric signal; and
a lens cover that is disposed to cover the plurality of detection elements and that has an optical function of setting an optical axis of an infrared ray incident from a specific detection point as a focal position of each detection element, and
wherein the intensity of the electric signal corresponding to the sensitivity for monitoring the moving object is proportional to the number of detection elements detecting the infrared rays.

* * * * *